(12) United States Patent
Hashimoto

(10) Patent No.: US 11,565,984 B2
(45) Date of Patent: Jan. 31, 2023

(54) PRODUCTION APPARATUS AND PRODUCTION METHOD OF TRIPTANE

(71) Applicant: Honda Motor Co. Ltd., Tokyo (JP)

(72) Inventor: Kohtaro Hashimoto, Wako (JP)

(73) Assignee: Honda Motor Co., Ltd., Tokyo (JP)

( * ) Notice: Subject to any disclaimer, the term of this patent is extended or adjusted under 35 U.S.C. 154(b) by 0 days.

(21) Appl. No.: 17/577,173

(22) Filed: Jan. 17, 2022

(65) Prior Publication Data

US 2022/0227684 A1 Jul. 21, 2022

(30) Foreign Application Priority Data

Jan. 20, 2021 (JP) .............................. JP2021-006889

(51) Int. Cl.
*C07C 1/24* (2006.01)
*C01B 32/05* (2017.01)
(Continued)

(52) U.S. Cl.
CPC ............... *C07C 1/24* (2013.01); *B01J 19/245* (2013.01); *C01B 32/05* (2017.08); *C01B 32/40* (2017.08);
(Continued)

(58) Field of Classification Search
None
See application file for complete search history.

(56) References Cited

U.S. PATENT DOCUMENTS 4,059,647 A * 11/1977 Wald .................... C07C 1/20
585/733
4,224,252 A  9/1980 Kyo et al.
(Continued)

FOREIGN PATENT DOCUMENTS

CN 107008502 B 8/2017
CN 110590489 A * 12/2019
(Continued)

OTHER PUBLICATIONS

Japanese Office action; Application No. 2021-006889; dated Sep. 13, 2022.

*Primary Examiner* — Ali Z Fadhel
(74) *Attorney, Agent, or Firm* — Duft & Bornsen, PC

(57) ABSTRACT

Production apparatus of triptane includes: carbon dioxide recovery unit configured to recover carbon dioxide from air; hydrogen generation unit configured to electrolyze water by renewable electricity to generate hydrogen; carbon monoxide generation unit configured to generate carbon monoxide from recovered carbon dioxide and hydrogen generated; methanol generation unit configured to generate methanol from carbon monoxide generated and hydrogen generated; acetic acid generation unit configured to generate acetic acid by reacting methanol generated with recovered carbon dioxide or with carbon monoxide generated; acetone generation unit configured to generate acetone and carbon dioxide from acetic acid generated; pinacolone generation unit configured to generate pinacolone from acetone generated; Grignard reagent generation unit configured to generate Grignard reagent from methanol generated; trimethyl butanol generation unit configured to generate 2,3,3-trimethyl-2-butanol by reacting pinacolone generated with Grignard reagent generated; and triptane generation unit configured to generate 2,2,3-trimethylbutane from 2,3,3-trimethyl-2-butanol generated.

4 Claims, 2 Drawing Sheets

(51) Int. Cl.
*C01B 32/40* (2017.01)
*B01J 19/24* (2006.01)
*C07C 29/151* (2006.01)
*C07C 51/12* (2006.01)
*C07C 45/68* (2006.01)
*C07F 3/02* (2006.01)
*C07C 29/132* (2006.01)
*C25B 1/04* (2021.01)
*C25B 15/08* (2006.01)
*C25B 9/17* (2021.01)
*C07C 45/41* (2006.01)

(52) U.S. Cl.
CPC ........ *C07C 29/132* (2013.01); *C07C 29/1518* (2013.01); *C07C 45/41* (2013.01); *C07C 45/68* (2013.01); *C07C 51/12* (2013.01); *C07F 3/02* (2013.01); *C25B 1/04* (2013.01); *C25B 9/17* (2021.01); *C25B 15/081* (2021.01); *B01J 2219/0004* (2013.01)

(56) References Cited

U.S. PATENT DOCUMENTS

2013/0210936 A1* 8/2013 Zhou .................. C07C 45/48
568/397
2016/0229777 A1 8/2016 Barnicki et al.

FOREIGN PATENT DOCUMENTS

| CN | 110590489 A | 12/2019 | | |
|---|---|---|---|---|
| JP | H04244035 A | 9/1992 | | |
| JP | 2005501894 A | 1/2005 | | |
| JP | 2011529497 A | 12/2011 | | |
| WO | 2020008505 A1 | 1/2020 | | |
| WO | WO-2020260607 A1 * | 12/2020 | ............... | C07C 1/24 |

* cited by examiner

PRODUCTION APPARATUS AND PRODUCTION METHOD OF TRIPTANE

CROSS-REFERENCE TO RELATED APPLICATION

This application is based upon and claims the benefit of priority from Japanese Patent Application No. 2021-006889 filed on Jan. 20, 2021, the content of which is incorporated herein by reference.

BACKGROUND OF THE INVENTION

Field of the Invention

This invention relates to a production apparatus and a production method of triptane.

Description of the Related Art

Conventionally, various production methods of triptane (2,2,3-trimethylbutane) are known (for example, see Japanese Unexamined Patent Application Publication No. 2005-501894 (JP2005-501894A)). In a production method described in JP 2005-501894 A, a cyclic hydrocarbon having 5 or 6 carbon atoms contained in naphtha is selectively ring-opened in the presence of hydrogen by a catalytic reaction and isomerized to produce triptane.

By the way, as a countermeasure against global warming, it is expected that methanol (renewable methanol) is synthesized using carbon dioxide recovered from a factory exhaust gas or the like and used for production of fuel such as gasoline. However, in the production method of JP2005-501894A, naphtha is used as a raw material, and therefore it is difficult to contribute to countermeasures against global warming.

SUMMARY OF THE INVENTION

An aspect of the present invention is a production apparatus of triptane, including: a carbon dioxide recovery unit configured to recover carbon dioxide from air to obtain a recovered carbon dioxide; a hydrogen generation unit configured to electrolyze water by renewable electricity to generate a hydrogen; a carbon monoxide generation unit configured to generate a carbon monoxide from the recovered carbon dioxide recovered by the carbon dioxide recovery unit and the hydrogen generated by the hydrogen generation unit; a methanol generation unit configured to generate a methanol from the carbon monoxide generated by the carbon monoxide generation unit and the hydrogen generated by the hydrogen generation unit; an acetic acid generation unit configured to generate an acetic acid by reacting the methanol generated by the methanol generation unit with the recovered carbon dioxide recovered by the carbon dioxide recovery unit or with the carbon monoxide generated by the carbon monoxide generation unit; an acetone generation unit configured to generate an acetone and a carbon dioxide from the acetic acid generated by the acetic acid generation unit; a pinacolone generation unit configured to generate a pinacolone from the acetone generated by the acetone generation unit; a Grignard reagent generation unit configured to generate a Grignard reagent from the methanol generated by the methanol generation unit; a trimethyl butanol generation unit configured to generate a 2,3,3-trimethyl-2-butanol by reacting the pinacolone generated by the pinacolone generation unit with the Grignard reagent generated by the Grignard reagent generation unit; and a triptane generation unit configured to generate a 2,2,3-trimethylbutane from the 2,3,3-trimethyl-2-butanol generated by the trimethyl butanol generation unit.

Another aspect of the present invention is a production method of triptane, including: a carbon dioxide recovery process configured to recover carbon dioxide from air to obtain a recovered carbon dioxide; a hydrogen generation process configured to electrolyze water by renewable electricity to generate a hydrogen; a carbon monoxide generation process configured to generate a carbon monoxide from the recovered carbon dioxide recovered in the carbon dioxide recovery process and the hydrogen generated in the hydrogen generation process; a methanol generation process configured to generate a methanol from the carbon monoxide generated in the carbon monoxide generation process and the hydrogen generated in the hydrogen generation process; an acetic acid generation process configured to generate an acetic acid by reacting the methanol generated in the methanol generation process with the recovered carbon dioxide recovered in the carbon dioxide recovery process or with the carbon monoxide generated in the carbon monoxide generation process; an acetone generation process configured to generate an acetone and a carbon dioxide from the acetic acid generated in the acetic acid generation process; a pinacolone generation process configured to generate a pinacolone from the acetone generated in the acetone generation process; a Grignard reagent generation process configured to generate a Grignard reagent from the methanol generated in the methanol generation process; a trimethyl butanol generation process configured to generate a 2,3,3-trimethyl-2-butanol by reacting the pinacolone generated in the pinacolone generation process with the Grignard reagent generated in the Grignard reagent generation process; and a triptane generation process configured to generate a 2,2,3-trimethylbutane from the 2,3,3-trimethyl-2-butanol generated in the trimethyl butanol generation process.

BRIEF DESCRIPTION OF THE DRAWINGS

The objects, features, and advantages of the present invention will become clearer from the following description of embodiments in relation to the attached drawings, in which.

DETAILED DESCRIPTION OF THE INVENTION

Hereinafter, an embodiment of the present invention will be described with reference to FIGS. 1A and 1B. A production apparatus of triptane according to an embodiment of the present invention produces triptane (2,2,3-trimethylbutane) using renewable methanol as a raw material.

The average global temperature is maintained in a warm range suitable for organisms by greenhouse gases in the atmosphere. Specifically, part of the heat radiated from the ground surface heated by sunlight to outer space is absorbed by greenhouse gases and re-radiated to the ground surface, whereby the atmosphere is maintained in a warm state.

Increasing concentrations of greenhouse gases in the atmosphere cause a rise in average global temperature (global warming).

Carbon dioxide is a greenhouse gas that greatly contributes to global warming, and its concentration in the atmosphere depends on the balance between carbon fixed on or in the ground in the form of plants or fossil fuels and carbon present in the atmosphere in the form of carbon dioxide. For example, carbon dioxide in the atmosphere is absorbed through photosynthesis in the growth process of plants, causing a decrease in the concentration of carbon dioxide in the atmosphere. Carbon dioxide is also released into the atmosphere through combustion of fossil fuels, causing an increase in the concentration of carbon dioxide in the atmosphere. In order to mitigate global warming, it is necessary to replace fossil fuels with renewable energy sources such as sunlight, wind power, and biomass to reduce carbon emissions.

Therefore, in the present embodiment, a production apparatus and a production method of triptane will be described in which renewable methanol is synthesized using carbon dioxide recovered from a factory exhaust gas or the like, and triptane serving as a modifier for gasoline is produced using the renewable methanol as a raw material.

Figure 1A:
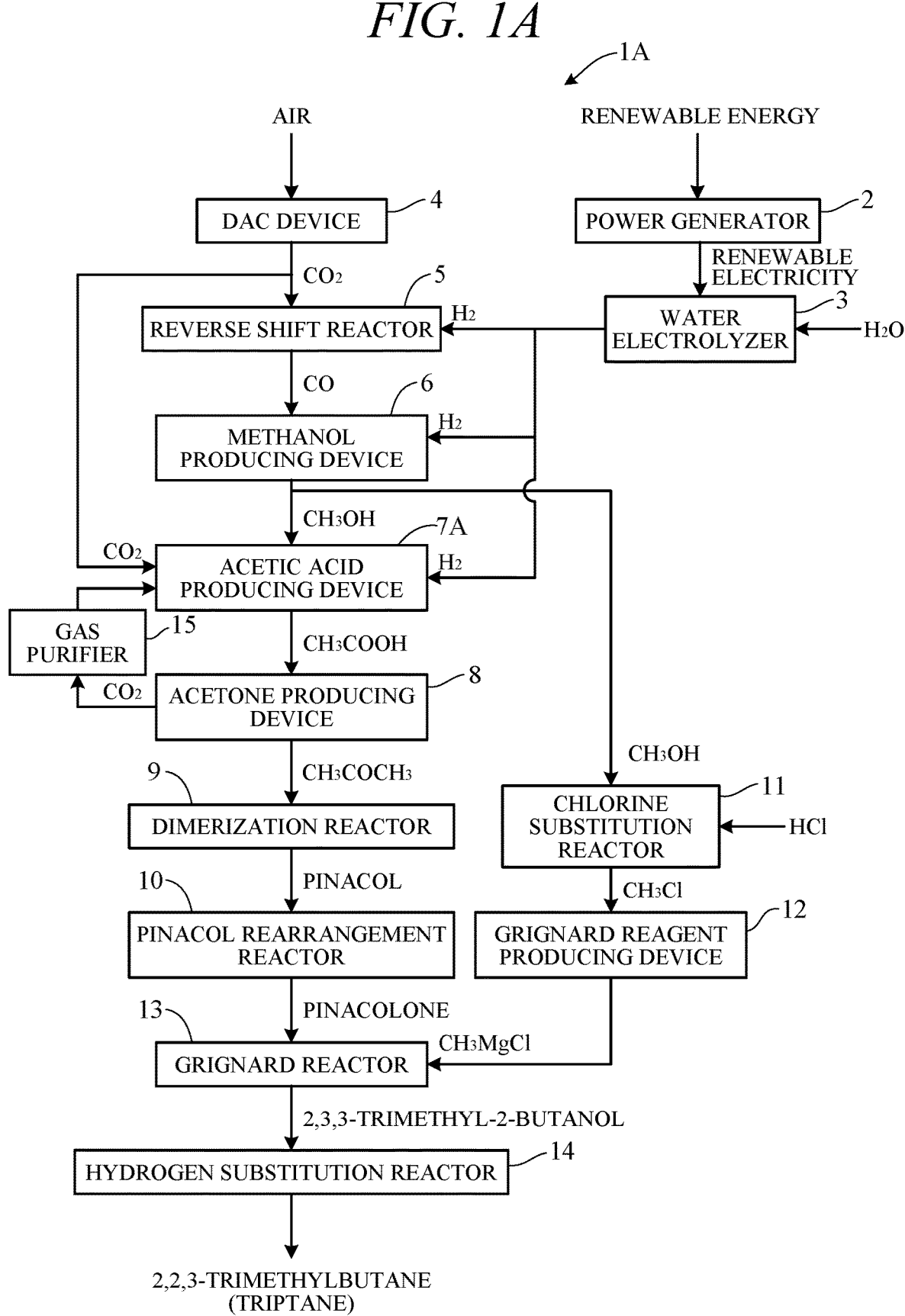
FIG. 1A is a block diagram schematically showing an example of configuration of a production apparatus of triptane according to an embodiment of the present invention.

FIG. 1A is a block diagram schematically illustrating an example of a configuration of a production apparatus of triptane (hereinafter, referred to as production apparatus) 1A according to an embodiment of the present invention. As illustrated in FIG. 1A, the production apparatus 1A includes a power generator 2, a water electrolyzer 3, a DAC device 4, a reverse shift reactor 5, a methanol producing device 6, an acetic acid producing device 7A, an acetone producing device 8, a dimerization reactor 9, a pinacol rearrangement reactor 10, a Grignard reactor 13, a hydrogen substitution reactor 14, a chlorine substitution reactor 11, a Grignard reagent producing device 12, and a gas purifier 15.

The power generator 2 is constituted as, for example, a solar power generator that converts solar energy into electric energy by a semiconductor element or a wind power generator that converts wind energy into electric energy by a wind turbine, and generates renewable electricity.

The water electrolyzer 3 electrolyzes water with renewable electricity generated by the power generator 2 to generate hydrogen (renewable hydrogen) ($H_2$).

The direct air capture (DAC) device 4 separates and recovers carbon dioxide ($CO_2$) as a so-called carbon neutral carbon source from a raw material gas (air) containing carbon dioxide such as a factory exhaust gas by, for example, a chemical absorption method. Specifically, the raw material gas is selectively absorbed in an absorbent such as an amine, and the absorbent is heated to separate and recover high-purity carbon dioxide. For a pump for transporting the raw material gas and the absorbent and a heater for heating the absorbent, renewable electricity generated by the power generator 2 is used.

To the reverse shift reactor 5, carbon dioxide recovered by the DAC device 4 and hydrogen generated by the water electrolyzer 3 are supplied, and the reverse shift reactor 5 generates carbon monoxide (CO) and water ($H_2O$) by a reverse shift reaction (equilibrium reaction) of the following formula (i) at 600 to 700° C. in the presence of a catalyst such as copper or nickel. Unreacted carbon dioxide in the reverse shift reactor 5 is supplied to a subsequent acetic acid production step. For a heater for heating the reverse shift reactor 5, renewable electricity generated by the power generator 2 is used. An yield of carbon monoxide in this reaction is about 67% at 700° C., but can be further enhanced under a hydrogen excess condition, and can be, for example, 100%.

$$CO_2 + H_2 \rightarrow CO + H_2O \qquad (i)$$

To the methanol producing device 6, carbon monoxide generated by the reverse shift reactor 5 and hydrogen generated by the water electrolyzer 3 are supplied, and the methanol producing device 6 generates methanol ($CH_3OH$) by a reaction of the following formula (ii) at 240 to 260° C. and 50 to 100 atm in the presence of a copper-zinc catalyst. For a heater for heating the methanol producing device 6 and a pump for pressurization, renewable electricity generated by the power generator 2 is used. An yield of methanol in this reaction is about 95%.

$$CO + 2H_2 \rightarrow CH_3OH \qquad (ii)$$

To the acetic acid producing device 7A, methanol generated by the methanol producing device 6, hydrogen generated by the water electrolyzer 3, and carbon dioxide (unreacted in the reverse shift reactor 5) recovered by the DAC device 4 are supplied, and the acetic acid producing device 7A generates acetic acid ($CH_3COOH$) by a reaction of the following formula (iii) at 200° C. and 100 atm in the presence of a ruthenium-rhodium catalyst. For a heater for heating the acetic acid producing device 7A and a pump for pressurization, renewable electricity generated by the power generator 2 is used. An yield of acetic acid in this reaction is about 77%.

$$CH_3OH + H_2 + CO_2 \rightarrow CH_3COOH + H_2O \qquad (iii)$$

To the acetone producing device 8, acetic acid generated by the acetic acid producing device 7A is supplied, and the acetone producing device 8 generates acetone ($CH_3COCH_3$), carbon dioxide, and water by a reaction of the following formula (iv) at 325° C. at normal pressure in the presence of a chromium-zinc-manganese catalyst. For a heater for heating the acetone producing device 8, renewable electricity generated by the power generator 2 is used. An yield of acetone in this reaction is about 96%.

$$2CH_3COOH \rightarrow CH_3COCH_3 + CO_2 + H_2O \qquad (iv)$$

To the dimerization reactor 9, acetone generated by the acetone producing device 8 is supplied, and the dimerization reactor 9 generates pinacol (($CH_3$)$_2$COHCOH($CH_3$)$_2$) by a pinacol coupling reaction of the following formula (v) in the presence of a catalyst such as magnesium.

$$2CH_3COCH_3 \rightarrow (CH_3)_2COHCOH(CH_3)_2 \qquad (v)$$

To the pinacol rearrangement reactor 10, pinacol generated by the dimerization reactor 9 is supplied, and the pinacol rearrangement reactor 10 generates pinacolone (($CH_3$)$_3$CCOCH$_3$) by a pinacol rearrangement reaction of the following formula (vi) under a strongly acidic condition. Since the substituents of pinacol are all methyl groups ($CH_3$), only pinacolone is obtained by the rearrangement reaction from pinacol.

$$(CH_3)_2COHCOH(CH_3)_2 \rightarrow (CH_3)_3CCOCH_3 \qquad (vi)$$

To the chlorine substitution reactor 11, methanol generated by the methanol producing device 6 and hydrogen chloride (HCl) are supplied, and the chlorine substitution reactor 11 generates chloromethane ($CH_3Cl$) and water by a reaction of the following formula (vii) in the presence of a catalyst such as zinc under a heating condition. For a heater for heating the chlorine substitution reactor 11, renewable electricity generated by the power generator 2 is used.

$$CH_3OH + HCl \rightarrow CH_3Cl + H_2O \qquad (vii)$$

To the Grignard reagent producing device 12, chloromethane generated by the chlorine substitution reactor 11 and metallic magnesium (Mg) are supplied, and the Grignard reagent producing device 12 generates Grignard reagent ($CH_3MgCl$) by a reaction of the following formula (viii) in an ether or tetrahydrofuran (THF) solvent.

$$CH_3Cl + Mg \rightarrow CH_3MgCl \qquad (viii)$$

To the Grignard reactor 13, pinacolone generated by the pinacol rearrangement reactor 10 and Grignard reagent generated by the Grignard reagent producing device 12 are supplied, and the Grignard reactor 13 generates 2,3,3-trimethyl-2-butanol (($CH_3)_3CC(CH_3)_2OH$) by a Grignard reaction of the following formula (ix). The Grignard reaction is irreversible.

$$(CH_3)_3CCOCH_3 + CH_3MgCl \rightarrow (CH_3)_3CC(CH_3)_2OH + HOMgCl \qquad (ix)$$

To the hydrogen substitution reactor 14, 2,3,3-trimethyl-2-butanol generated by the Grignard reactor 13 is supplied, and the hydrogen substitution reactor 14 halogenates and then reduces 2,3,3-trimethyl-2-butanol to generate 2,2,3-trimethylbutane (triptane) (($CH_3)_3CC(CH_3)_2$), for example, as in the following formula (x).

$$(CH_3)_3CC(CH_3)_2OH \rightarrow (CH_3)_3CC(CH_3)_2X \rightarrow (CH_3)_3CC(CH_3)_2 \qquad (x)$$

To the gas purifier 15, carbon dioxide generated as an intermediate product by the acetone producing device 8 is supplied, and the gas purifier 15 purifies the supplied carbon dioxide gas. The carbon dioxide purified by the gas purifier 15 is supplied to the acetic acid producing device 7A. That is, to the acetic acid producing device 7A, in addition to the carbon dioxide recovered by the DAC device 4 and unreacted in the reverse shift reactor 5, the carbon dioxide purified by the gas purifier 15 is supplied. As described above, by recirculating the carbon dioxide obtained as an intermediate product, the carbon neutral carbon source recovered by the DAC device 4 can be effectively used without discharging carbon dioxide as the entire production apparatus 1A.

Figure 1B:
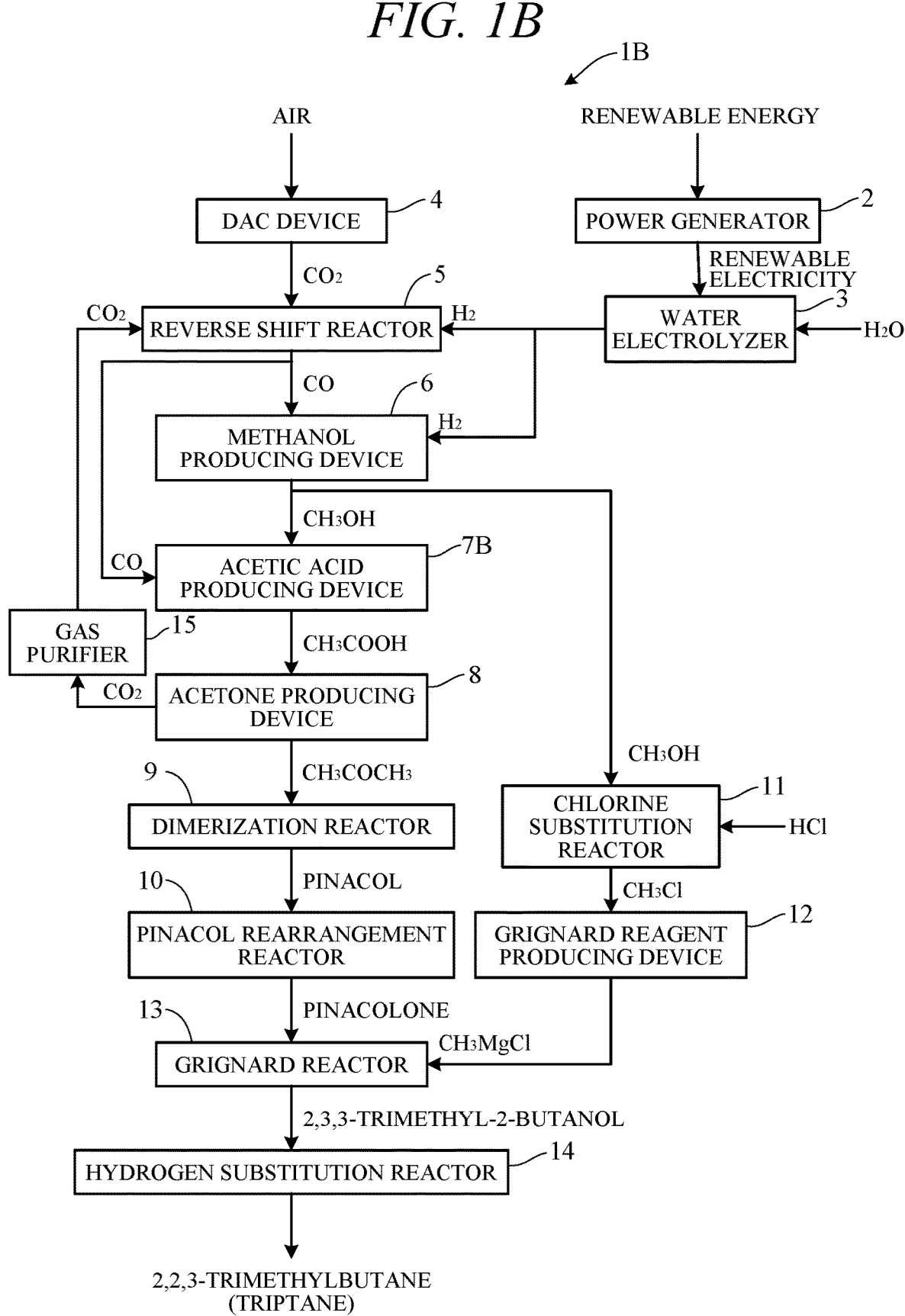
FIG. 1B is a block diagram schematically showing another example of configuration of the production apparatus of triptane according to the embodiment of the present invention.

FIG. 1B is a block diagram schematically illustrating an example of a configuration of a production apparatus 1B which is a modification of the production apparatus 1A of FIG. 1A. To an acetic acid producing device 7B of the production apparatus 1B, methanol generated by the methanol producing device 6 and carbon monoxide generated by the reverse shift reactor 5 are supplied, and the acetic acid producing device 7B generates acetic acid by a reaction of the following formula (xi) at 200° C. and 30 atm in the presence of a rhodium or iridium catalyst. For a heater for heating the acetic acid producing device 7B and a pump for pressurization, renewable electricity generated by the power generator 2 is used.

$$CH_3OH + CO \rightarrow CH_3COOH \qquad (xi)$$

The carbon dioxide purified by the gas purifier 15 of the production apparatus 1B is supplied to the reverse shift reactor 5. That is, to the reverse shift reactor 5, in addition to the carbon dioxide recovered by the DAC device 4, the carbon dioxide purified by the gas purifier 15 is supplied. As described above, by recirculating the carbon dioxide obtained as an intermediate product, the carbon neutral carbon source recovered by the DAC device 4 can be effectively used without discharging carbon dioxide as the entire production apparatus 1B.

The present embodiment can achieve advantages and effects such as the following:

(1) The apparatus 1A, 1B includes: the DAC device 4 configured to recover carbon dioxide from the air; the water electrolyzer 3 configured to electrolyze water by the renewable electricity to generate hydrogen; the reverse shift reactor 5 configured to generate carbon monoxide from the recovered carbon dioxide and generated the hydrogen; the methanol producing device 6 configured to generate methanol from the generated carbon monoxide and the generated hydrogen; the acetic acid producing device 7A, 7B configured to generate acetic acid by reacting the generated methanol with the recovered carbon dioxide or with the generated carbon monoxide; the acetone producing device 8 configured to generate acetone and carbon dioxide from the generated acetic acid; the dimerization reactor 9 and the pinacol rearrangement reactor 10 configured to generate pinacolone from the generated acetone; the chlorine substitution reactor 11 and the Grignard reagent producing device 12 configured to generate Grignard reagent from the generated methanol; the Grignard reactor 13 configured to generate 2,3,3-trimethyl-2-butanol by reacting the generated pinacolone with the generated Grignard reagent; and the hydrogen substitution reactor 14 configured to generate 2,2,3-trimethylbutane from the generated 2,3,3-trimethyl-2-butanol (FIG. 1A, FIG. 1B).

By producing triptane serving as a modifier for gasoline using, as a raw material, renewable methanol synthesized using carbon dioxide as a carbon neutral carbon source recovered from a factory exhaust gas or the like, the carbon strength of reformed gasoline can be reduced to contribute to countermeasures against global warming.

(2) The production apparatus 1A further includes: the gas purifier 15 configured to purify the carbon dioxide generated by the acetone producing device 8 (FIG. 1A). The acetic acid producing device 7A generates the acetic acid by reacting the methanol generated by the methanol producing device 6 with the carbon dioxide recovered by the DAC device 4 and the carbon dioxide purified by the gas purifier 15 (FIG. 1A). By recirculating the carbon dioxide obtained as an intermediate product, the carbon neutral carbon source can be effectively used without discharging carbon dioxide as the entire production apparatus 1A.

(3) The production apparatus 1B further includes: the gas purifier 15 configured to purify the carbon dioxide generated by the acetone producing device 8 (FIG. 1B). The reverse shift reactor 5 generates the carbon monoxide by reacting the carbon dioxide recovered by the DAC device 4 and the carbon dioxide purified by the gas purifier 15 with the hydrogen generated by the water electrolyzer 3 (1B). The acetic acid producing device 7B generates the acetic acid by reacting the methanol generated by the methanol producing device 6 with the carbon monoxide generated by the reverse shift reactor 5 (1B). By recirculating the carbon dioxide obtained as an intermediate product, the carbon neutral carbon source can be effectively used without discharging carbon dioxide as the entire production apparatus 1B.

In the above embodiment, the example of using the DAC device 4 that recovers carbon dioxide in a raw material gas by a chemical absorption method has been described, but the carbon dioxide recovery unit that recovers carbon dioxide in air is not limited to such a unit. For example, a pressure swing adsorption (PSA) method may be used in which carbon dioxide is selectively adsorbed to an adsorbent such as activated carbon or zeolite, and the carbon dioxide is separated and recovered by decompression.

In the above embodiment, a catalyst, a reagent, a reaction condition, and the like for generating carbon monoxide, methanol, acetic acid, acetone, pinacolone, Grignard reagent, 2,3,3-trimethyl-2 butanol, and 2,2,3-trimethylbutane have been exemplified, but the catalyst, the reagent, the reaction condition, and the like are not limited to those exemplified above.

The above embodiment can be combined as desired with one or more of the above modifications. The modifications can also be combined with one another.

According to the present invention, it becomes possible to contribute to countermeasures against global warming.

Above, while the present invention has been described with reference to the preferred embodiments thereof, it will be understood, by those skilled in the art, that various changes and modifications may be made thereto without departing from the scope of the appended claims.

What is claimed is:

1. A production apparatus of triptane, comprising:
   a carbon dioxide recovery unit configured to recover carbon dioxide from air to obtain a recovered carbon dioxide;
   a hydrogen generation unit configured to electrolyze water by renewable electricity to generate a hydrogen;
   a carbon monoxide generation unit configured to generate a carbon monoxide from the recovered carbon dioxide recovered by the carbon dioxide recovery unit and the hydrogen generated by the hydrogen generation unit;
   a methanol generation unit configured to generate a methanol from the carbon monoxide generated by the carbon monoxide generation unit and the hydrogen generated by the hydrogen generation unit;
   an acetic acid generation unit configured to generate an acetic acid by reacting the methanol generated by the methanol generation unit with the recovered carbon dioxide recovered by the carbon dioxide recovery unit or with the carbon monoxide generated by the carbon monoxide generation unit;
   an acetone generation unit configured to generate an acetone and a carbon dioxide from the acetic acid generated by the acetic acid generation unit;
   a pinacolone generation unit configured to generate a pinacolone from the acetone generated by the acetone generation unit;
   a Grignard reagent generation unit configured to generate a Grignard reagent from the methanol generated by the methanol generation unit;
   a trimethyl butanol generation unit configured to generate a 2,3,3-trimethyl-2-butanol by reacting the pinacolone generated by the pinacolone generation unit with the Grignard reagent generated by the Grignard reagent generation unit; and
   a triptane generation unit configured to generate a 2,2,3-trimethylbutane from the 2,3,3-trimethyl-2-butanol generated by the trimethyl butanol generation unit.

2. The production apparatus of triptane according to claim 1, further comprising:
   a carbon dioxide purification unit configured to purify the carbon dioxide generated by the acetone generation unit to obtain a purified carbon dioxide, wherein
   the acetic acid generation unit generates the acetic acid by reacting the methanol generated by the methanol generation unit with the recovered carbon dioxide recovered by the carbon dioxide recovery unit and the purified carbon dioxide purified by the carbon dioxide purification unit.

3. The production apparatus of triptane according to claim 1, further comprising:
   a carbon dioxide purification unit configured to purify the carbon dioxide generated by the acetone generation unit to obtain a purified carbon dioxide, wherein
   the carbon monoxide generation unit generates the carbon monoxide by reacting the recovered carbon dioxide recovered by the carbon dioxide recovery unit and the purified carbon dioxide purified by the carbon dioxide purification unit with the hydrogen generated by the hydrogen generation unit, wherein
   the acetic acid generation unit generates the acetic acid by reacting the methanol generated by the methanol generation unit with the carbon monoxide generated by the carbon monoxide generation unit.

4. A production method of triptane, comprising:
   a carbon dioxide recovery process configured to recover carbon dioxide from air to obtain a recovered carbon dioxide;
   a hydrogen generation process configured to electrolyze water by renewable electricity to generate a hydrogen;
   a carbon monoxide generation process configured to generate a carbon monoxide from the recovered carbon dioxide recovered in the carbon dioxide recovery process and the hydrogen generated in the hydrogen generation process;
   a methanol generation process configured to generate a methanol from the carbon monoxide generated in the carbon monoxide generation process and the hydrogen generated in the hydrogen generation process;
   an acetic acid generation process configured to generate an acetic acid by reacting the methanol generated in the methanol generation process with the recovered carbon dioxide recovered in the carbon dioxide recovery process or with the carbon monoxide generated in the carbon monoxide generation process;
   an acetone generation process configured to generate an acetone and a carbon dioxide from the acetic acid generated in the acetic acid generation process;
   a pinacolone generation process configured to generate a pinacolone from the acetone generated in the acetone generation process;
   a Grignard reagent generation process configured to generate a Grignard reagent from the methanol generated in the methanol generation process;
   a trimethyl butanol generation process configured to generate a 2,3,3-trimethyl-2-butanol by reacting the pinacolone generated in the pinacolone generation process with the Grignard reagent generated in the Grignard reagent generation process; and
   a triptane generation process configured to generate a 2,2,3-trimethylbutane from the 2,3,3-trimethyl-2-butanol generated in the trimethyl butanol generation process.

* * * * *